Figure 1:
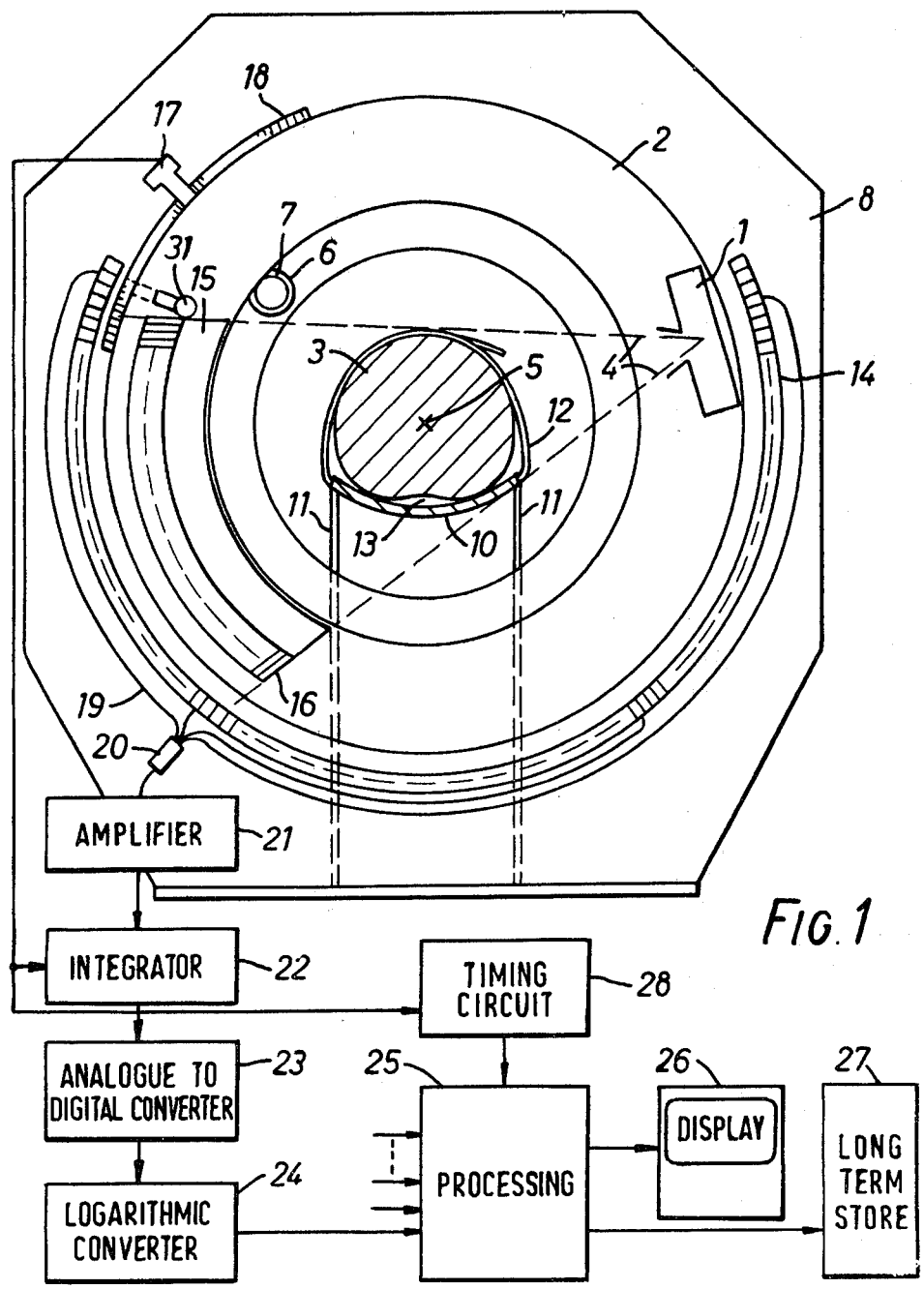

United States Patent [19]

Oliver

[11] 4,298,799
[45] Nov. 3, 1981

[54] RADIOGRAPHY

[75] Inventor: Colin C. Oliver, Langley, England

[73] Assignee: EMI Limited, Hayes, England

[21] Appl. No.: 897,789

[22] Filed: Apr. 19, 1978

Related U.S. Application Data

[62] Division of Ser. No. 772,689, Feb. 28, 1977.

[30] Foreign Application Priority Data

Mar. 3, 1976 [GB] United Kingdom ............... 8417/76

[51] Int. Cl.³ .............................................. G03B 41/16
[52] U.S. Cl. ............................... 250/445 T; 250/360; 250/505; 250/509
[58] Field of Search ................... 250/445 T, 360, 505, 250/508, 509

[56] References Cited

U.S. PATENT DOCUMENTS 4,048,503  9/1977  Taylor .............................. 250/445 T
4,057,725  11/1977  Wagner .......................... 250/445 T

OTHER PUBLICATIONS

"AS&E CT Scanner," American Science and Engineering, Cambridge, Mass. 1976.

Primary Examiner—Craig E. Church
Attorney, Agent, or Firm—Cooper, Dunham, Clark, Griffin & Moran

[57] ABSTRACT

In a computerized tomographic radiographic apparatus a source directs a fan distribution of radiation through a patient to be detected by a bank of detector devices. The detector devices are disposed on a circular path centered on an axis about which the source orbits. The detectors are fixed relative to the body so that the radiation is incident on different detectors as the source orbits. Each detector devices receives radiation in different orientations, in the fan distribution, at different times.

9 Claims, 3 Drawing Figures

RADIOGRAPHY

This is a division of application Ser. No. 772,689 filed Feb. 28, 1977.

The present invention relates to radiography, and it relates more especially to that branch of radiography which has become known as computerises axial tomography, or briefly C.A.T. Apparatus for performing C.A.T. has the aim of evaluating the absorption coefficient, with respect to the radiation used, at each of a plurality of locations distributed over a planar slice disposed in a body under examination.

The evaluation is usually performed by suitably processing signals indicative of the absorption suffered by the radiation on traversing each of many substantially linear beam paths through the body in the plane of the slice. To obtain the required signals, it is usual to scan a source of radiation relative to the body and to detect the radiation emergent from the side of the body opposite the source whilst the source assumes many different positions relative to the body, as described in one example given in U.S. Pat. No. 3,778,614.

If it is desired to acquire the signals rapidly, it is convenient to use a source of a fan-shaped, planar spread of radiation which encompasses at least a substantial part of the slice; the planes of the spread of radiation and of the slice being conincident. Such a spread may be a continuous fan of radiation or may if desired be split up by collimators between the body and the source. An array of detector devices is disposed at the opposite side of the body to the source so that each detects the radiation emergent from the body along a respective beam path, the paths being divergent, and the source and the detector devices are rotated around the body about a common axis substantially perpendicular to the plane of the slice and of the spread of radiation, so as to provide signals relating to the absorption suffered by the radiation on traversing further groups of beam paths; signals relating to many groups of beam paths being obtained on rotation of the source and the detector devices through for example an angle exceeding 180° by about the angle of the fan or radiation. Such a technique is described and claimed in U.S. application No. 481,443. Preferably the signals are sorted into sets relating to substantially parallel beam paths and are processed, a set at a time, by the technique disclosed and claimed in U.S. Pat. No. 3,924,129, due allowance being made for the fact that the parallel beam paths are not uniformly spaced across the slice. U.S. Pat. No. 3,778,614 and U.S. application No. 481,443 and U.S. Pat. No. 3,924,129 are hereby incorporated herein by reference. It will be understood that the data need not be sorted into sets of parallel beam paths provided processing appropriate to fan distributions of beam paths is used.

A difficulty arises, however, due to the tendency of different detector devices to drift in gain relative to one another during the time taken to acquire the signals, i.e. the scanning time. Since a given detector always provides signals relating to beam paths at a constant perpendicular distance from the axis of rotation, such drifting causes the superposition of ring-shaped artifacts upon the evaluated coefficients.

It is an object of this invention to reduce the above-mentioned difficulty.

According to the invention there is provided radiographic apparatus including at least one source adapted to project a fan-shaped spread of penetrating radiation through a slice of the body of a patient, means for angularly moving said at least one source relative to the body about an axis intersecting the slice so as to project the radiation through the body from a plurality of different directions, a bank of detector devices disposed along a circular path centred on said axis, said detectors being substantially fixed relative to the body and extending around said circular path to an extent which subtends at the axis an angle substantially equal to or greater than the sum of 180° and the angle subtended by the fan-shaped spread at the source; wherein the means for moving is adapted to move the said at least one source to an extent sufficient to irradiate each of said detector devices with radiation which has traversed the body.

Figure 2A:
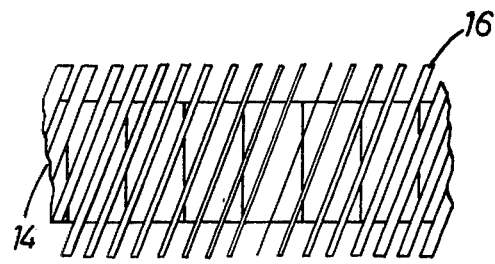
Figure 2B:
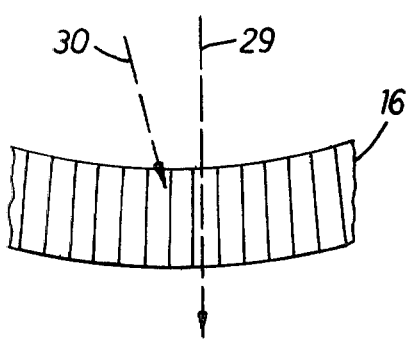
Figure 3:
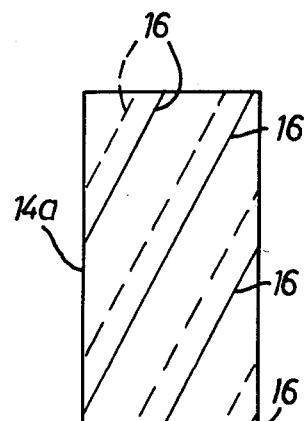

In order that the invention may be clearly understood and readily carried into effect, one embodiment thereof will now be described, by way of example only, with reference to the accompanying drawings of which FIG. 1 shows, is schematic front elevational view, apparatus in accordance with one example of the invention, FIG. 2 shows the relationship of collimator baffle plates to the detector devices, and FIG. 3 is a diagram used to explain the principles of the collimator baffle plates.

Referring to the drawing, an X-ray tube 1, typically a rotating anode tube of conventional construction, is mounted on an angularly movable ring 2 so as to irradiate a part 3 of a patient's body. The tube 1 is arranged to produce a substantially planar, fan-shaped spread 4 of X-radiation, and the body is positioned so that the part 3, which represents a cross-sectional slice over which the absorption coefficients are to be evaluated is in the plane of the spread 4. The angular motion of the ring 2 occurs about an axis 5 which is disposed, in this example, substantially centrally of the body part 3 and is perpendicular to the plane of the spread 4. The motive force for effecting the angular movement of the ring 2 is an electric motor 6 which drives a gear wheel 7. The latter co-operates with gear teeth formed all around the inner periphery of the ring 2. Motor 6 is mounted on a stationary main frame 8 concentric with the ring 2 and sufficiently large to enable the body to pass therethrough in a supine position. The body is supported on a bed 10, which itself is supported as at 11 on either side of the scanning gantry, and secured thereto by means of a strap 12. Packing material 13, which may contain water or viscous or particulate material in one or more plastic bags, is placed between the body and the bed 10 in the region of examination so as to reduce the entrapment of air between the body part 3 and the bed 10. The material 13 preferably absorbs the X-radiation to a similar extent as does human tissue.

The main frame 8 also supports a bank 14 of detector devices; the devices being disposed on a circular path concentric with, but of larger radius than, the ring 2, i.e. centred on axis 5. The array extends over an angle which, in this example, substantially equals the sum of 180° and the fan angle. Since the angle of the fan-shaped spread 4 of radiation is 40° in this example, the extent of the detector array 14 is approximately 220°. This extent is necessary in order that signals may be obtained relating to sets containing equal numbers of parallel beam paths distributed over substantially 180° as is required for highly accurate operation if the signals are to be processed in accordance with the technique described and claimed in the aforementioned U.S. Pat. No.

3,924,129. If desired the detector array may extend over the full 360°.

Each detector device in the array 14 typically comprises a scintillator crystal, for example thallium activated caesium iodide, together with a light sensitive element such as a photomultiplier tube or a photo diode. Between the detector array 14 and the body is disposed a collimator arrangement 15, 16, to reduce scatter incident upon the detector devices. The element 15 of the collimator arrangement comprising a pair of plates disposed parallel to the plane of the spread 4 of radiation and the element 16 comprising a baffle consisting of a plurality of collimator plate which are parallel to one another in one direction and inclined to the junction lines between adjacent detector crystals as will be explained in more detail hereinafter. The baffle 16, while reducing the amount of incident scattered radiation, does not define a precise angle of incidence for each individual detector. This enables the detector devices to receive radiation projected along various beams within the spread 4 as the radiation is scanned over the devices during the angular movement of the ring 2. The pitch of the baffle plates is not necessarily related to the distance between corresponding parts of adjacent detector devices, however it is typically of the same magnitude as or less than the detector pitch.

The detector devices in some parts of the array 14 have to be capable of receiving radiation from any angle within the spread 4 and thus each detector is arranged to view the source through an aperture having a 40° field of view.

It will be appreciated that allowance has to be made, in determining the placing of the detector devices, for the fact that the circular path upon which the detector devices are located is of larger diameter than the trajectory of the effective point source of radiation. In one example, 660 detectors are provided, angularly spaced by $\frac{1}{3}$° in relation to axis 5.

In operation, the active scan commences with the fan in a position to irradiate a group of detectors at one extreme of array 14 and the ring 2, and with it the source 1, is angularly moved around the body part 3 about axis 5. Clearly, as the angular movement proceeds, the radiation sweeps around the detector array 14; the output signals provided by the devices of array 14 being sampled at a rate determined by timing pulses produced by the co-operation of a photocell unit 17, mounted on the stationary frame 8, and a graticule 18 mounted on the ring 2. At regular intervals one detector device at the rear end of the spread 4 is substituted by a new detector device at the forward end of the spread 4, so that samples are at all times provided by the same number of detectors. In order to save expense, detectors spaced apart by more than the fan angle, i.e. detectors which cannot be irradiated at the same time, can share photomultipliers and/or subsequent electrical circuits on a time division basis. The scan is terminated when all detectors have been irradiated by radiation which has passed through the body.

Such an arrangement is shown in the drawing; detectors spaced apart in angle by more than 40° being coupled, via fibre-optic light guides such as 19 to a common photomultiplier such as 20 and each photomultiplier being arranged to feed a respective channel comprising an amplifier such as 21, an integrator such as 22 which is read and reset periodically by the aforementioned timing pulses, an analogue to digital converter circuit such as 23 and a logarithmic converter circuit such as 24. All of the logarithmic converter circuits such as 24 feed a processing circuit 25 which is arranged to sort the signals applied thereto into sets relating to parallel beam paths through the body part 3, to adjust the signals to take account of the aforementioned non-uniformity of spacing of the parallel beam paths and to process the signals so sorted and adjusted in accordance with the technique described and claimed in the aforementioned patent application to evaluate the absorption coefficient at each of a plurality of locations distributed over the slice comprising the body part 3. Preferably the coefficients so evaluated are displayed on a visual display such as a cathode ray tube 26, which has facilities for photographing the display thereon, and also supplied to a long term store 27. Store 27 is preferably a magnetic tape or disc store. The time division multiplexing of the various photomultipliers and subsequent channels of electrical circuits is effected under the influence of a timing circuit 28 which receives the aforementioned timing pulses and develops further timing signals which operate gates in the circuit 25 to route the various signals to their correct locations.

The arrangement of the baffles 16 is shown schematically in plan view in FIG. 2a and, in the same elevation as FIG. 1, in FIG. 2b. Part of the detector array 14 is also shown. As in FIG. 1, the baffles and detectors are each disposed on circles centred on the axis 5 and the junctions between individual detectors are on radii from that axis. The baffles 16 are, however, radial to the origin of the X-rays so that they intercept directly transmitted radiation as little as possible. For the same reason they are relatively thin. In this way they allow direct radiation, such as 29, to pass to the detectors with little loss but tend to intercept scattered radiation, such as 30. The junction between individual detectors is intended to include a plane lying midway between adjacent detectors which may not be in actual physical contact.

It is nevertheless not possible to prevent the baffles 16 intercepting at least some radiation directly transmitted from the source. Furthermore the baffles 16, in the course of rotation about axis 5, move relative to the detectors 14. If the output readings from each detector are to be of equal significance it is necessary to ensure that each detector loses the same proportion of radiation, to any baffles disposed in its path, in each sampling period of an integrator. Clearly, for baffles parallel to the junctions between detectors (i.e. in a direction perpendicular to the paper in FIG. 2b), the timing of the integrators must be carefully regulated to achieve that effect. In certain circumstances an error of timing equivalent to a circumferential movement of the thickness of one baffle plate could lead to an error which may be unacceptable.

The arrangement of FIG. 2 therefore disposes the baffles 16 so that they are inclined to the junctions between detectors in the said direction. The amount of baffle overlying each detector during an integration period is then constant, despite timing errors, provided that the inter baffle spacing is not too large.

FIG. 3 illustrates the relationship for one detector crystal 14a, which is shielded by several baffles 16 to the extent indicated by the solid lines. If the baffles move relative to the detector to the position indicated by the broken lines it can be seen that the total baffle length, shielding the detector, is substantially the same.

It will be understood that other shapes and dispositions of baffles may be used, for example s-shaped or chevron-shaped, provided the baffles present substantially the same exit aperture for the radiation to each detector device despite their relative movement. That effect requires that when the proportion of any baffle overlying a detector device increases, the overlying proportion of another baffle should decrease the substantially the same extent. The pitch of the baffle must be sufficiently short to give that effect.

Of course baffles may be disposed parallel to the junction lines between detectors of the integrator timing is precisely controlled as indicated hereinbefore.

As the fan-shaped spread 4 of radiation is more than sufficient to embrace the breadth of the body part 3 in the examination plane, each detector receives, at least once during the examination, radiation directly from the source 1. The output signals obtained at these times are used as calibration signals to check the sensitivity of the detectors.

If the body is too large in some or all dimensions to permit the calibration referred to above to be effected for all detector devices, an auxiliary source 31 can be mounted on the ring 2 beyond one extreme of the fan of radiation and used to irradiate the detector devices directly (i.e. not through the body) to enable calibration signals to be obtained. The auxiliary source 31 may be an X-ray tube or a radioisotope source and may project radiation at the detector devices along a single pencil-like beam or along a fan-like spread. It is, of course, necessary to take account of the presence of the auxiliary source when deciding which detector devices can share photomultipliers etc. If necessary, the auxiliary radiation can be of different energy distribution than the main source 1 so that information relating to the two sources, if fed into a common channel, can be separated on an energy basis, such separation being well known in the art.

In a further embodiment of the invention more than one X-ray source such as 1 may be provided to irradiate the entire detector array in the course of a lesser angular motion.

It will be understood that suitable collimator arrangements different than that shown in FIGS. 2 and 3, can be used in conjunction with this invention.

What I claim is:

1. Radiographic apparatus, for examining a body, including a least one x-ray tube projecting a fan-shaped distribution of x-rays through a slice of the body, means for angularly moving the at least one x-ray tube relative to the body about an axis intersecting the slice to cause the x-ray tube to project radiation through the body from a plurality of different directions, and a plurality of detector devices disposed along a curved path around the body, to an extent which subtends at the axis an angle substantially equal to or greater than 180° and fixed so as to be substantially prevented from angular movement around the body, in the direction of motion of the source, wherein the means for moving moves the said at least one x-ray tube to an extent sufficient to irradiate each of the detector devices, and including collimators moving angularly around the body together with the x-ray tube relative to the fixed detectors to reduce the incidence on the detectors of radiation transmitted through the body along indirect paths.

2. Radiographic apparatus, for examining a body, including at least one source projecting a fan-shaped distribution of penetrating radiation through a slice of the body, means for angularly moving said at least one source relative to the body, about an axis intersecting the slice, to cause the source to project the radiation through the body from a plurality of different directions, and a plurality of detector devices disposed along a curved path around said body, wherein the detectors are fixed so as to be substantially prevented from angular movement around the body, in the direction of motion of the source, and extend around the curved path to an extent which subtends at the axis an angle substantially equal to or greater than 180°, where the means for angularly moving the said at least one source moves the source angularly to an extent sufficient to irradiate the detector devices with radiation which has traversed the body and the extent of the fan-shaped distribution is sufficient to cause each detector to receive, at least once during the examination, radiation, from the source, which has not passed through the body.

3. Apparatus according to claim 2 wherein the extent of the fan-shaped distribution is such that the radiation extends beyond the body to provide, at the edge of the distribution, radiation which has not passed through the body and which is successively received by the detectors, as the angular movement proceeds, to provide detector outputs suitable for use in calibration.

4. Apparatus according to claim 2 including collimators moving angularly around the body together with the source relative to the detectors to reduce the incidence on the detectors of radiation transmitted along indirect paths.

5. Radiographic apparatus according to claim 4 in which the at least one source of radiation is a single collimated x-ray tube and the means for angularly moving the source orbits the x-ray tube around the body to be examined.

6. Radiographic apparatus, for examining a body, including at least one source projecting a fan-shaped distribution of penetrating radiation through a slice of the body, means for angularly moving said at least one source relative to the body, about an axis intersecting the slice, to cause the source to project the radiation through the body from a plurality of different directions, and a plurality of detector devices disposed along a curved path around said body, wherein the detectors are fixed so as to be substantially prevented from angular movement around the body, in the direction of movement of the source, and extend around the curved path to an extent which subtends at the axis an angle substantially equal to or greater than 180°, and wherein the extent to which the means for angularly moving moves the at least one source and the extent of the fan-shaped distribution are such that individual detector devices receive, at different times, radiation from the source along paths which traverse the body and paths which do not traverse the body.

7. A medical radiographic system for examining a patient comprising a circular array of x-ray detectors surrounding the patient and an x-ray tube which moves relative to the array of x-ray detectors and around the patient along a circular path concentric with the detector array and is collimated to emit a fan beam of x-radiation which passes through the patient and simultaneously illuminates a number of said x-ray detectors, the spread of said fan being more than sufficient to embrace the patient and each of said detectors receiving, at least once during examination of a patient, x-radiation directly from the x-ray tube rather than through the patient, said x-ray detectors providing, in response to said directly received x-radiation, output signals for use as calibration signals for the x-ray detectors, each detector additionally receiving, at other times, radiation which has passed through the patient.

8. A medical radiographic system as in claim 7 including collimators located between the patient and the x-ray detectors and moving around the patient with the x-ray tube, said collimators reducing the incidence of scattered x-radiation on the x-ray detectors.

9. A medical radiographic system for examining a patient as in claim 7 in which each of said detectors receives x-radiation directly from the x-ray tube rather than through the patient at least twice during the examination of a patient, once before that detector starts receiving radiation which has passed through the patient and once after that detector stops receiving radiation which has passed through the patient, each of said x-ray detectors providing in response to the radiation received directly from the x-ray tube both before and after the detector has received radiation which has passed through the patient, output signals for use as calibration signals for the x-ray detectors.

* * * * *